United States Patent [19]

Folz et al.

[11] 3,995,035

[45] Nov. 30, 1976

[54] 6-AMINO-2-LOWER-ALKYL-4-NITROPYRIDINE N-OXIDE COMPOSITIONS AND COCCIDIOSTAT PROCESS

[75] Inventors: Sylvester D. Folz; Joseph J. Ursprung, both of Kalamazoo, Mich.

[73] Assignee: The Upjohn Company, Kalamazoo, Mich.

[22] Filed: Dec. 18, 1974

[21] Appl. No.: 533,990

Related U.S. Application Data

[63] Continuation of Ser. No. 154,177, June 17, 1971, abandoned.

[52] U.S. Cl. .............................. 424/246; 424/248; 424/263; 260/243 B; 260/247.5 G; 260/293.69; 260/296 R
[51] Int. Cl.$^2$ ..................... A01N 9/22; A61K 31/44
[58] Field of Search ................ 260/296 R; 424/263, 424/246, 248

[56] References Cited
UNITED STATES PATENTS 2,531,756    11/1950   Waletzky et al. ............... 260/296 R
3,495,969    2/1970    Driscoll .................................. 71/94

OTHER PUBLICATIONS

Talik (I), Chemical Abstracts, vol. 60, col. 2884 (1964), (abst. of Bull. Acad. Polon, Sci. Ser. Sci. vol. 9 pp. 561–565, (1961)).

Talik (II), Chemical Abstracts vol. 57, cols. 15065 to 15066 (1962), (abst. of Roczniki Chem. vol. 35, pp. 475 to 488 (1961)).

*Primary Examiner*—John D. Randolph
*Attorney, Agent, or Firm*—John J. Killinger; Roman Saliwanchik

[57] ABSTRACT

Certain new 6-amino-2-lower-alkyl-4-nitropyridine N-oxides, particularly 6-amino-4-nitro-2-picoline N-oxide, have been found to be effective coccidiostats. The amino group can be varied and acid addition and quaternary ammonium salts are included.

14 Claims, No Drawings

6-AMINO-2-LOWER-ALKYL-4-NITROPYRIDINE N-OXIDE COMPOSITIONS AND COCCIDIOSTAT PROCESS

This is a continuation of application Ser. No. 154,177, filed June 17, 1971, now abandoned.

SUMMARY OF THE INVENTION

This invention pertains to new organic chemical compounds, a process for preparing the same, a new method for controlling pestiferous protozoa therewith, and new formulations of the compounds. The invention is more particularly directed to new 6-amino-2-lower-alkyl-4-nitropyridine N-oxides, a process for preparing the same, a new method for controlling pestiferous, pathogenic (parasitic) protozoa in animals with the 6-amino-2-lower-alkyl-4-nitropyridine N-oxides and new formulations thereof for administering to animals.

The new 6-amino-2-lower-alkyl-4-nitropyridine N-oxides of this invention have the general structural formula:

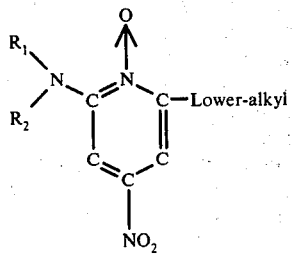

wherein lower-alkyl is of from 1 to 6 carbon atoms, inclusive; and the amino group

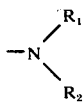

is more fully described as follows:

The variables $R_1$ and $R_2$ are independently hydrogen; lower-alkyl of from 1 to 6 carbon atoms, inclusive; and lower-alkenyl of from 3 to 6 carbon atoms, inclusive; but taken together constitute, with the nitrogen atom, a saturated heterocyclic amino group of from 5 to 7 ring members, inclusively, having a total of not more than 15 carbon atoms.

The acid addition and quaternary ammonium salts thereof constitute a further embodiment of the invention.

The foregoing 6-amino-2-lower-alkyl-4-nitropyridine N-oxides of Formula I are patentably new even though they might have been recognized in the generic class of "Substituted Nitropyridines . . . " proposed in U.S. Pat. No. 3,495,969. This limited and special class of compounds were barely discernible in an obscure and unilluminated area of the patent disclosure.

Referring to the patent's general formula at column 2, lines 65 through 71 and the definitions at column 3, lines 1 through 25, the compounds are recognizable if the following multiplicity of selections of variables are made. The variable $m$ must be selected to be 1 and that single nitro group must be attached at the 4-position; the variable F is selected to be 1 from among 0, 1, or 2; and the resulting variable

must be $NH_2$, $N(alkyl)_2$, or $N\text{-}(alkenyl)_2$ and must be further attached at the 6-position; the variable $n$ is selected to be 1; X is selected to be alkyl, and the alkyl group is attached at the 2-position. In order to make the foregoing selections meaningful, the variable $q$ must be selected to be 1 in order to recognize the N-oxides of this invention.

A pertinent question attends the foregoing multiplicity of selections. Did the patentees indicate them? An answer is that no N-oxide is shown in the specification or included in the claims, only one p-nitro compound is shown (No. 45), and this compound is characterized by a p-chlorophenoxy group in the ortho-position. The p-chlorophenoxy group is clearly unrelated to either an alkyl group or the amino group. One concludes therefore that the reference patent does not really provide those skilled in the art with a disclosure of or procedure for making 6-amino-2-lower-alkyl-4-nitropyridine N-oxides according to this invention. Hence, the compounds of this invention were in an obscure and unilluminated area of the prior art and not known to be active against protozoa.

The phrase "lower-alkyl of from 1 to 6 carbon atoms, inclusive;" includes methyl, ethyl, propyl, butyl, pentyl, hexyl, and isomeric forms thereof. The phrase "lower-alkenyl of from 3 to 6 carbon atoms, inclusive;" includes for example allyl, 1-methallyl, 2-methallyl, 2-butenyl (crotyl), 3-butenyl, 1,2-dimethallyl, 1,1,-dimethallyl, 2-ethylallyl, 1-methyl-1-butenyl, 2-methyl-2-butenyl, 3-methyl-2-butenyl, 3-pentenyl, 2,3-dimethyl-2-butenyl, 1,1,2-trimethylallyl, 1,3-dimethyl-2-butenyl, 1-ethyl-2-butenyl, 4-methyl-2-pentenyl, 4-hexenyl, and the like.

The phrase "saturated heterocyclic amino group of from 5 to 7 ring members, inclusively," includes for example pyrrolidinyl, lower-alkylpyrrolidinyl, for example, 2-methylpyrrolidinyl, 3-butylpyrrolidinyl, and 2-isohexylpyrrolidinyl, polylower-alkylpyrrolidinyl, for example, 2,3-di-methylpyrrolidinyl, 2,2-dimethylpyrrolidinyl, 2,5-diethylpyrrolidinyl, and 2,3,5-trimethylpyrrolidinyl, piperidino, lower-alkylpiperidino, for example, 2-methylpiperidino, 3-methylpiperidino, 4-methylpiperidino, 3-isopropylpiperidino, and 4-tert-butylpiperidino, polylower-alkylpiperidino, for example, 3,4-diethylpiperidino, 2-methyl-5-ethylpiperidino, 3,5-dipentylpiperidino, 2,4,6-trimethylpiperidino, and 2,3,5-triethylpiperidino, hexamethyleneimino, loweralkylhexamethyleneimino, for example 2-ethylhexamethyleneimino, 4-tert-butylhexamethyleneimino, and 3-heptylhexamethyleneimino, polylower-alkylhexamethyleneimino, for example, 2,4-dimethylhexamethyleneimino, 3,3-dimethylhexamethyleneimino, 2,4,6-tripropylhexamethyleneimino, and 2,2-dibutylhexamethyleneimino, 4-lower-alkylpiperazinyl, for example, 4-methylpiperazinyl and 4-isopropylpiperazinyl, polylower-alkylpiperazinyl, for example 2,2,4,5,5-pentamethylpiperazinyl, and 2,4,5-trimethylpiperazinyl, morpholino, lower-alkylmorpholino, for example, 2-ethylmorpholino and 3-isobutylmorpholino, polyloweralkylmorpholino, for example, 2-ethyl-5-methylmorpholino, 3,3-dimethylmorpholino, and 2,6-di-tertbutylmorpholino, thiamorpholino, lower-alkylthiamorpholino, for example, 3-methylthiamorpholino, and polylower-alkylthiamorpholino, for example, 2,3,6-trimethylthiamorpholino and 2,3,5,6-tetramethylthiamorpholino.

The foregoing specified and many other like saturated heterocyclic amino groups are contemplated as being within the scope of this invention. It will be noted that the saturated amino heterocycle can be other than cycloalkyleneimino and there can be a second hetero atom in the ring, i.e., an oxygen atom, a sulfur atom, or a second nitrogen atom as a ring member. In general, the second hetero atom is preferably in the 4-position of a six-membered ring, but it can be in the 3-position. Accordingly, it will be recognized that the "taken together" concept can be alkylene, oxadialkylene, e.g.,

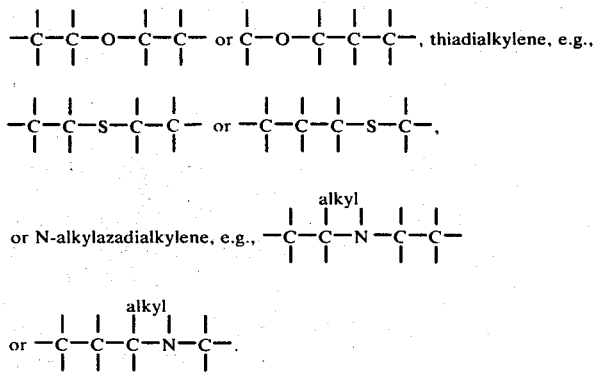

DETAILED DESCRIPTION OF THE INVENTION

Protozoa are ubiquitous, primitive animals that are microscopic in size. Parasitic protozoa have become dependent upon other animals for sustenance, and, when they occur in large numbers, frequently interfere with growth and development of their various hosts. Sporozoans are a specialized group of parasitic protozoans that produce disease in many kinds of animals, particularly domestic and wild animals including all kinds of poultry, cattle, sheep, horses, rabbits, goats, swine, mink, raccoon, and foxes. The coccidia are forms of Sporozoans.

The general name for the disease condition resulting from unchecked reproduction of coccidia is coccidiosis. A severely infected animal is characteristicly unthrifty, emaciated, debilitated, and ultimately comatose. Mortality can be very high if the animals (especially young ones) are predisposed by lack of previous exposure to coccidia, and the infecting dosage is relatively large. Sometimes, an exposed population develops a chronic high level of infection, and growth rate, egg production, or market finish is much reduced or delayed. Coccidia infect the cells lining the intestinal tract, destroy the cells, and thereby cause petechial hemorrhages that result in toxic anemia.

The 6-amino-2-lower-alkyl-4-nitropyridine N-oxides of this invention are active against protozoa and can be used prophylactically and therapeutically to prevent damage and losses. The compounds are conveniently administered to animals orally, although parenteral administration is contemplated. Orally, the compounds are provided in the feed, in the drinking water, in capsules, in tablets, in boluses, by drench, or via other forms known in the art of medicine. Parenteral administration is accomplished by intramuscular or intraperitoneal injection, subcutaneous implantation, or related techniques.

When coccidiosis in poultry (e.g., chickens) is to be prevented or treated, a 6-amino-2-lower-alkyl-4-nitropyridine N-oxide is conveniently dispersed homogeneously in the food or in the drinking water. In general, an effective amount is incorporated in a nutritionally complete ration so that there will be a relatively constant level of intake for normal birds that will prevent or at least curb severe infection. For chickens of the age 0 to 12 weeks (e.g., broiler production) the level of intake is contemplated in the range of 0.0001% to 0.1%, a preferred level being in the range of 0.004% to 0.03%. Illustratively, the compound 6-amino-4-nitro-2-picoline N-oxide gave complete control of coccidiosis when fed at the rate of 10 mg. per lb. of feed consumed.

When an outbreak of coccidiosis already exists in poultry and therapeutic treatment is required, the 6-amino-2-lower-alkyl-4-nitropyridine N-oxides of this invention can be administered in the drinking water or in an especially palatable feed so as to obtain larger than prophylactic dosages. For this purpose an acid addition salt of the invention can be dissolved in a quantity of water that will be consumed in a day. Concentrations can range from 0.06 g. to 0.6 g. per liter of water. Flavoring adjuvants such as monosodium glutamate, and surface active dispersing agents such as glycerol and sorbitan esters of fatty acids can be included.

Oral dosages for animals other than poultry also vary depending upon the kind of animal, age, weight, and physical condition. The amount of feed given per day must also be considered. For example, if feeding lambs are given 3 lbs. of supplement per day in a diet comprising fodder, the concentration of 6-amino-2-lower-alkyl-4-nitropyridine N-oxide can range appropriately from 0.001% to 0.05%. Similarly, rabbits fed a pelleted hay and grain ration as is commonly done nowadays, would appropriately be fed 0.0015% to 0.05% in the ration.

The acid addition and quaternary ammonium salt derivatives of the new 6-amino-2-lower-alkyl-4-nitropyridine N-oxide anti-protozoan agents are fully substitutable in the various formulations of the invention for the free base compounds of Formula I. Representative acid addition salts include the hydrochloride (preferred), the hydrobromide, they hydrogen sulfate, the phosphate, nitrate, acetate, propionate, benzoate, palmitate, succinate, gluconate, mucate, citrate, tartrate, pamoate, salicylates, cyclohexylsulfamates, and p-toluenesulfonate. Representative quaternary ammonium salts include the methochlorides, methobromides, propylchlorides, isopropylbromides, butyliodides, methoethanesulfonates, and metho 2-hydroxyethanesulfonates. The acid addition and quaternary amonium salts of the new 6-amino-2-lower-alkyl-4-nitropyridine N-oxides of this invention are prepared according to conventional methods including metathetic reactions involving interconvertible salts.

The new 6-amino-2-lower-alkyl-4-nitropyridine N-oxides of this invention, (Compounds according to Formula I, above) are prepared by reacting ammonia or an amine with a 6-halo-2-lower-alkyl-4-nitropyridine N-oxide. Starting compounds of this scope are contemplated by the reference patent, and 2-chloro-6-methyl-4-nitropyridine N-oxide is described by E. V. Brown, J. A. C. S. 79, p. 3565 (1957). The 6-halogen (preferably chlorine or bromine) is replaced by an amino group, and the compounds of the invention are thus obtained. Advantageously, the reaction is effected in a solvent medium when ammonia or lower-boiling amines such as methylamine or dimethylamine is selected as a reactant. When higher-boiling amines are reacted, for example, diisopropylamine, an excess of the amine itself can serve as a reaction medium. Suitable solvent media include alcohols, for example ethanol, isopropyl alcohol, ethylene glycol, and propylene glycol, and various polar solvents that will not react with amines, e.g., dimethylsulfoxide.

The substitution reaction is effected over a temperature range of 50° to 200° C. preferably about 80° to about 120° C. Since at these reaction temperatures, lower-boiling amines and ammonia volatilize readily, a sealed pressure-resistant reaction vessel is indicated for them. The reaction time varies in accordance with various factors, but 16–24, hrs. is suggested.

The desired 6-amino-2-lower-alkyl-4-nitropyridine N-oxide separates from the reaction mixture or otherwise can be recovered and purified by conventional methods. When there is original product separation as in Example 1, hereinbelow, filtration, washing and recrystallization will provide the desired chemical compound suitable for activity testing and ordinary use.

The 6-amino-4-nitropyridine-2-lower-alkyl N-oxide anti-protozoan agents of this invention (compounds according to Formula I) but preferably the specific compound 6-amino-4-nitro-2-picoline N-oxide can be administered to animals in many forms for the purpose of controlling pestiferous, parasitic protozoa. The pure compounds can be used if desired, and technical grade compounds can also be used. In the interest of economy and flexibility, however, the compounds are preferably administered as formulations characterized by a greater or less proportion of a physiologically acceptable, accessory material. The foregoing phrase "physiologically acceptable, accessory material" as used in this specification is intended to include all of the various liquids, e.g., water, ethanol and physiological saline solution; solids, e.g., finely divided talc, starches, and clays; and possibly adjuvants, e.g., surfactants, preservatives, and spreaders that in general are known by those skilled in the art and useful for dilution of a pure or technical grade active agent or for effectuating the action of the agent.

Under some circumstances of administration, e.g., oral administration in a food or in drinking water, the physiologically acceptable accessory material, illustratively a nutritionally complete ration, a supplemental ration for use with forage, or the water itself will constitute a major proportion of the total formulation with minor even to the point of relative infinitisimal proportion of the active ingredient. On the other hand, oral administration in a capsule, tablet, bolus, or drench might have a major, substantial, or moderate proportion of the active agent. The principal criterion is an effective amount considering concentration and total amount consumed.

Under other circumstances of administration, e.g., intraperitoneally, intramuscularly, subcutaneously, or even intravenously the physiologically acceptable accessory material, i.e., a fluid material suitable for injection, will constitute a major, substantial, or moderate proportion of the formulation.

Accordingly, a wide range of proportions (or concentrations of 6-amino-2-lower-alkyl-4-nitropyridine N-oxides) is contemplated. Provisionally, a useful range of concentrations is between 0.001 per cent and 98 per cent. A preferred range is between 0.010 per cent and 40 per cent. The precise concentration needed for a particular circumstance of administration depends upon the protozoan to be controlled, the animal host, the rationale of treatment (whether therapeutic or prophylactic), the stage of disease development (whether acute or chronic), and last but not least, the physical condition of the host animal.

The following examples are illustrative of the process and products of the present invention but are not to be construed as limiting. The parts and percentages are by weight and the solvent ratios are by volume unless otherwise specified.

EXAMPLE 1

Preparation of 6-amino-4-nitro-2-picoline N-oxide and hydrochloride thereof

A reaction solution consisting of 5.66 g. (0.03 mole) 6-chloro-4-nitro-2-picoline N-oxide and 100 ml. ethanol was saturated with anhydrous ammonia and sealed in a strong bottle. This reaction mixture was heated and maintained at a temperature in the range of 100° to 105° C. for 21 hrs. The bottle and contents were then cooled and the seal was broken. Crystals had formed. The crystals were collected on a filter and washed with a small amount of cold ethanol. Recrystallization from 95% aqueous ethanol yielded 2.06 g. (41% yield) of 6-amino-4-nitro-2-picoline N-oxide as yellow needles having a melting point at 221° to 222° C. (with decomposition). When a small sample was mixed with ethanolic ferric chloride a blue solution was obtained.

Analysis: Calc'd for $C_6H_7N_3O_3$: C, 42.61; H, 4.17; N, 24.84. Found: C, 43.42; H, 3.80; N, 23.97. I.R.: NH: 3440; unsat. CH: 3220, 3170, 3110; C=C/C=N/NH def: 1665, 1645, 1570, $NO_2$: 1535, 1345, C-N: 1220, 1085. U.V.: (ethanol: 210(18,350); 235 (11,150); 265 (8,250); 319 (5,100 ); 390 (4,800).

A solution consisting of 1.69 g. (0.01 mole) 6-amino-4-nitro-2-picoline N-oxide and 75 ml. methanol was heated to the boiling point and 1 ml. concentrated hydrochloric acid (0.012 mole) was added. After heating the acidified solution until evaporation of the methanol had reduced its volume to about 25 ml., it was cooled to 25° C. Solids separated. The solids were collected on a filter and rinsed on the filter first with cold methanol and then with cold ether. There was thus obtained 1.27 g. of 6-amino-4-nitro-2-picoline N-oxide hydrochloride having a melting point at 188° to 189° C.

EXAMPLE 2

Following the procedure of Example 1, but substituting separately methylamine, ethylamine, isopropylamine, pentylamine, hexylamine, dimethylamine, diethylamine, dipropylamine, N-methyl-tert-butylamine, N-ethylhexylamine, dihexylamine, allylamine, diallylamine, di-2-butenylamine, di-4-hexenylamine, pyrrolidine, piperidine, morpholine, thiamorpholine, hexamethyleneimine, and 2-methylpyrrolidine for anhydrous ammonia, there is prepared the corresponding 6-methylamino-4-nitro-2-picoline N-oxide,
6-ethylamino-4-nitro-2-picoline N-oxide,
6-isopropylamino-4-nitro-2-picoline N-oxide,
4-nitro-6-pentylamino-2-picoline N-oxide,
6-hexylamino-4-nitro-2-picoline N-oxide,
6-dimethylamino-4-nitro-2-picoline N-oxide, 6-diethylamino-4-nitro-2-picoline N-oxide,
4-nitro-6-dipropylamino-2-picoline N-oxide,
6-(methyl-tert-butylamino)-4-nitro-2-picoline N-oxide,
6-(ethylhexylamino)-4-nitro-2-picoline N-oxide,
6-dihexylamino-4-nitro-2-picoline N-oxide,
6-allylamino-4-nitro-2-picoline N-oxide,
6-diallylamino-4-nitro-2-picoline N-oxide,
6-di(2-butenyl)amino-4-nitro-2-picoline N-oxide,
6-di(4-hexenyl)amino-4-nitro-2-picoline N-oxide,
4-nitro-6-pyrrolidinyl-2-picoline n-oxide,
4-nitro-6-piperidino-2-picoline N-oxide,
6-morpholino-4-nitro- 2-picoline N-oxide,
4-nitro-6-thiamorpholino-2-picoline N-oxide,
6-hexamethyleneimino-4-nitro-2-picoline N-oxide,
6(2-methylpyrrolidinyl)-4-nitro-2-picoline N-oxide,
6-(2-methylpyrrolidinyl)-4-nitro-2-picoline N-oxide, respectively.

EXAMPLE 3

Following the procedure of Example 1, but substituting separately 6-chloro-2-ethyl-4-nitropyridine N-oxide, 6-chloro-2-propyl-4-nitropyridine N-oxide, 6-chloro-2-isopropyl-4-nitropyridine N-oxide, 2-n-butyl-6-chloro-4-nitropyridine N-oxide, 6-chloro-2-tert-butyl-4-nitropyridine N-oxide, 6-chloro-2-n-pentyl-4-nitropyridine N-oxide, and 6-chloro-2-n-hexyl-4-nitropyridine N-oxide for 6-chloro-4-nitro-2-picoline N-oxide, there is prepared the corresponding
6-amino-2-ethyl-4-nitropyridine N-oxide,
6-amino-2-propyl-4-nitropyridine N-oxide,
6-amino-2-isopropyl-4-nitropyridine N-oxide,
6-amino-2-n-butyl-4-nitropyridine N-oxide,
6-amino-2-tert-butyl-4-nitropyridine N-oxide,
6-amino-2-n-pentyl-4-nitropyridine N-oxide,
6-amino-2-n-hexyl-4-nitropyridine N-oxide, respectively.

EXAMPLE 4

The compound 6-amino-4-nitro-2-picoline N-oxide was administered to growing chicks 21 days old at the rates of 0.025% and 0.0125% (by weight) in a nutritionally adequate diet. After 36 hrs. consuming this diet (premedication interval), the chicks were inoculated with Eimeria tenella at the rate of 100,000 sporulated oocysts per bird by oral intubation. A measured amount of inoculum, standardized by hemocytometer counts according to the method of William E. Bray (1957), (Clinical Laboratory Methods, 5th Ed., Mosby, St. Louis, Mo.) was administered from a syringe.

Feeding the medicated diet was continued for 7 days when the experiment was terminated. According to the results, the medicated chicks were protected from mortality (100% of the chicks survived), and their weight gains (132.0 g. mean for both males and females) was relatively comparable to the survival (100%) and weight gains (142.5 g. mean) of unmedicated, uninfected controls. The feed efficiency of the test group was determined to be 1.97 g. feed/g. gain which compares favorably with the control group's feed efficiency of 1.88 g. feed/g. gain. A similar group of chicks unmedicated, but also infected with the standardized inoculum of E. tenella suffered 80% mortality.

Representative protozoa include, for example, those of the Order Eucoccidia, Class Telesporea, and Subphylum Sporozoa; illustratively, coccidia which attack and parasitize the cells lining the intestinal tracts of animals such as Eimeria bovis, E. zurnii, and E. ellipsoidalis in cattle; E. ahsata, E. arloingi, E. faursi, and E. parva in sheep and goats; E. debliecki, E. scabra, and E. suis in swine; Isospora bigemina, l. felis, E. canis, and E. felina in dogs and cats; E. tenella, E. necatrix, E. acervulina, E. maxima, and E. meleagrimitis in poultry; E. stiedae, and E. perforans in rabbits; and E. mustelae in mink. The compound 6-amino-4-nitro-2-picoline N-oxide is active against Ochromonas danica.

Representative nutritionally complete rations for most common domestic animals can be found described in Feeds and Feeding, 23rd Ed. (1959) by Morrison and Morrison (Comstock Publishing Co., Ithaca, New York). An authority about poultry rations is W. R. Ewing's Poultry Nutrition, 5th rev. Ed. (1963) printed by Ray Ewing Co., Division of Hoffman LaRoche, Inc., Pasadena, California, 1475 pp. Still another authority is Nutrition of the Chicken by M. L. Scott, M. C. Nesheim, and R. J. Young (1969), 511 pp., published by M. L. Scott and Assoc. Publishers, Ithaca, New York. These and other sources available in academic and other libraries throughout the world will provide appropriate selections of rations as vehicles for the anti-protozoal agents of this invention.

Representative physiologically acceptable fluids for injection can be found described in Merck Veterinary Manual, 3rd ed., 1967, Merck and Company, Rahway, New Jersey, and Joseph P. Remington Pharmaceutical Sciences, 14th ed., 1970, Mack Publishing Co., Easton, Pennsylvania. Preferred ones are physiological saline, water, dextrose, vegetable oils, mixtures of water with polymers, suspending agents, polyvinylpyrrolidone, dimethylacetamide, and the like.

We claim:
1. The method of controlling coccidia in animals which comprises administering to animals an effective anti-coccidial amount of an active ingredient comprising one or more 6-amino-2-lower-alkyl-4-nitropyridine N-oxides of the formula:

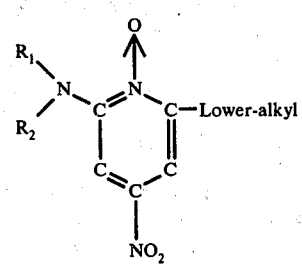

wherein lower-alkyl is of from 1 to 6 carbon atoms, inclusive; and the amino group

is more fully described as follows:
The variables $R_1$ and $R_2$ are independently hydrogen; lower-alkyl of from 1 to 6 carbon atoms, inclusive; and lower-alkenyl of from 3 to 6 carbon atoms, inclusive; but taken together constitute, with the nitrogen atom, a saturated heterocyclic amino group of from 5 to 7 ring members, inclusively, having a total of not more than 15 carbon atoms, provided that the second hetero atom is selected from the group consisting of O, S, or N, including acid addition and quaternary ammonium salts thereof.

2. The method according to claim 1 wherein "lower-alkyl" is methyl.

3. The method according to claim 1 wherein $R_1$ and $R_2$ are hydrogen.

4. The method according to claim 2 wherein the active ingredient is the compound 6-amino-4-nitro-2-picoline N-oxide.

5. Formulations for effecting control of coccidia in animals comprising an effective anticoccidial amount of one or more 6-amino-2-lower-alkyl-4-nitropyridine N-oxides of the formula:

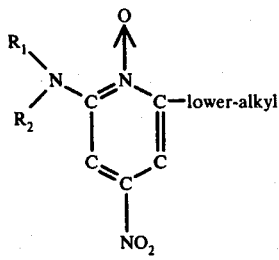

wherein lower-alkyl is of from 1 to 6 carbon atoms, inclusive; and the amino group

is more fully described as follows:

The variables $R_1$ and $R_2$ are independently hydrogen; lower-alkyl of from 1 to 6 carbon atoms, inclusive; and lower-alkenyl of from 3 to 6 carbon atoms, inclusive; but taken together constitute, with the nitrogen atom, a saturated heterocyclic amino group of from 5 to 7 ring members, inclusively, having a total of not more than 15 carbon atoms, provided that the second hetero atom is selected from the group consisting of O, S, or N, including acid addition and quaternary ammonium salts thereof and a physiologically acceptable accessory material.

6. Formulations according to claim 5, wherein "lower-alkyl" is methyl.

7. Formulations according to claim 5 wherein $R_1$ and $R_2$ are hydrogen.

8. Formulations according to claim 5 wherein the compound 6-amino-4-nitro-2-picoline N-oxide is present.

9. Formulations according to claim 5 wherein the physiologically acceptable accessory material is a complete ration for the animal, and the concentration of active agent is from 0.004% to 0.03%.

10. Formulations according to claim 5 wherein the physiologically acceptable accessory material is drinking water and the concentration of active agent is from 0.001% to 0.1%.

11. Formulations according to claim 5 wherein the physiologically acceptable accessory material is a finely divided solid.

12. Formulations according to claim 5 wherein the physiologically acceptable accessory material is a fluid.

13. Formulations according to claim 12 wherein the concentration of active agent is from 0.01% to 40.0%.

14. Formulations according to claim 11, in encapsulated form, wherein the concentration of active agent is from 0.01% to 40%.

* * * * *